United States Patent [19]
Hideki et al.

[11] Patent Number: 5,750,716
[45] Date of Patent: May 12, 1998

[54] METHOD OF PRODUCING PLATINUM (II) COMPLEX

[75] Inventors: Kawai Hideki; Imaoka Takayuki; Hata Go, all of Kanagawa, Japan

[73] Assignee: Toray Industries, Inc., Tokyo, Japan

[21] Appl. No.: 750,987

[22] PCT Filed: Apr. 25, 1996

[86] PCT No.: PCT/JP96/01142
  § 371 Date: Jan. 31, 1997
  § 102(e) Date: Jan. 31, 1997

[87] PCT Pub. No.: WO96/34000
  PCT Pub. Date: Oct. 31, 1996

[30] Foreign Application Priority Data

Apr. 25, 1995 [JP] Japan .................. 7/101226
May 9, 1995 [JP] Japan .................. 7/110854

[51] Int. Cl.$^6$ .................. C07D 205/00; C07F 15/00
[52] U.S. Cl. .................. 549/210; 556/137; 514/492
[58] Field of Search .................. 556/137; 549/210; 514/492

[56] References Cited

U.S. PATENT DOCUMENTS 5,616,613  4/1997  Kawai et al. .................. 514/492

*Primary Examiner*—Porfirio Nazario-Gonzalez
*Attorney, Agent, or Firm*—Birch, Stewart, Kolasch & Birch, L.L.P.

[57] ABSTRACT

The present invention relates to a method of producing a platinum (II) complex represented by the formula (A) below characterized by reacting a dichloroplatinum (II) complex represented by the formula (B) below and a tetronic acid derivative represented by the formula (C) below in the presence of a silver salt and a barium salt.

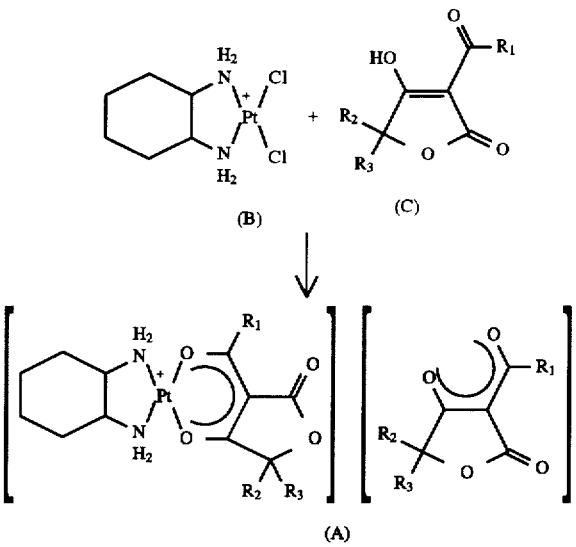

6 Claims, No Drawings

METHOD OF PRODUCING PLATINUM (II) COMPLEX

CROSS-REFERENCES TO RELATED APPLICATIONS

This application was filed as a request for U.S. examination under 35 U.S.C. § 371 of International application No. PCT/JP96/01142 filed Apr. 25, 1996.

TECHNICAL FIELD

The present invention relates to a method of producing the following platinum compound used as an anticancer drug.

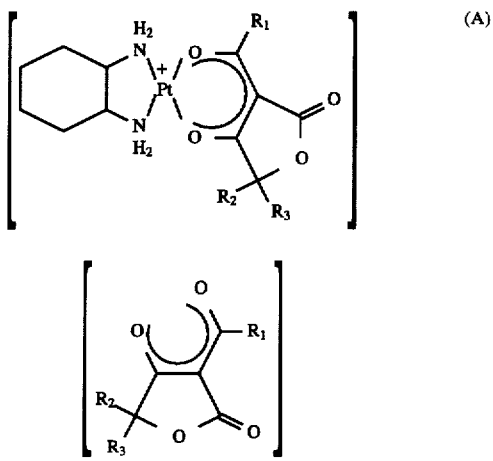

BACKGROUND ART

Methods of producing and purifying platinum compound (A) having anticancer activity are disclosed in the specification WO91009041. Namely, the production methods represented by the following formulae are disclosed.

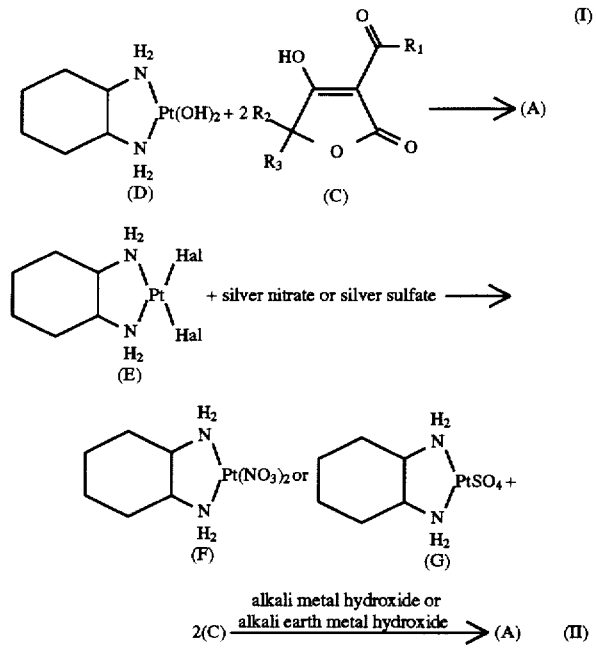

However, the above production method (I) has the problem that, although compound (D) used is produced by ion exchange of compound (F) using a strong anion-exchange resin, the strong anion-exchange resin is expensive and requires preparation for 3 to 5 days. The production method (II) has the problem that the two steps are required for obtaining compound (A). The methods disclosed in the specification WO91009041 have a yield of 60 to 65%.

An object of the present invention is to solve the above problems and provide a method which is capable of producing and purifying a platinum complex represented by formula (A) with high purity.

DISCLOSURE OF THE INVENTION

The present invention relates to a method of producing a platinum (II) complex represented by the following formula (A) comprising:

(A)

reacting a dichloroplatinum complex represented by the following formula (B), (B)

and a tetronic acid derivative represented by the following formula (C) in coexistence with a silver salt and a barium salt.

(C)

The present invention also relates to a method of improving the purity of optically active amines comprising mixing 1-trans-1,2-diaminocylcohexane or d-trans-1,2-diaminocylcohexane and an acid having no optically active point, and recrystallizing the resultant salt from a water-soluble organic solvent or a mixed solvent of water and a water-soluble organic solvent.

BEST MODE FOR CARRYING OUT THE INVENTION

The present invention is described with reference to preferred embodiments. It was found that a platinum complex represented by formula (A) can be produced by a one-step reaction in which equivalents or less of silver sulfate and barium hydroxide are reacted in water or a mixed solvent of water and an alcohol (methanol or ethanol) in the presence of platinum compound (B) and a compound represented by formula (C).

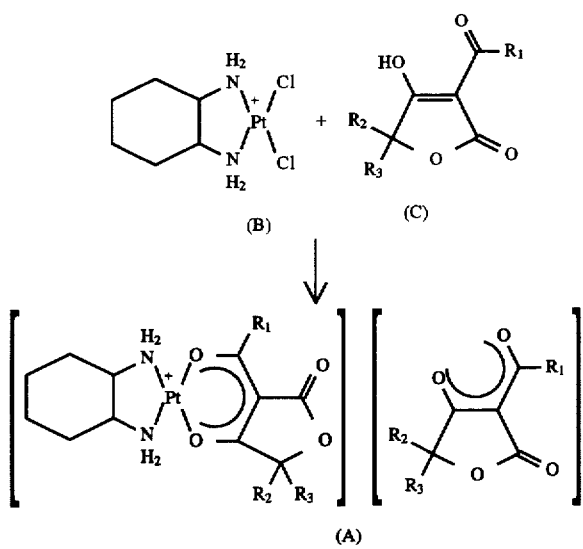

(In formulae (A) and (C), $R_1$ represents a lower hydrocarbon group having 1 to 3 carbon atoms, and $R_2$ and $R_3$ each represent a hydrogen atom or a lower hydrocarbon group having 1 to 3 carbon atoms.)

The construction of the present invention is described in detail below.

Although the barium salt used in the present invention is not limited, preferable examples of the barium salt include barium hydroxides such as barium hydroxide anhydride, barium hydroxide octahydrate, and the like. Of these hydroxides, barium hydroxide octahydrate is preferably used from the viewpoint of ease of procurement.

Although the silver salt used in the present invention is not limited, silver sulfate is preferably used. The silver salt is used in an amount of 0.7 to 1.0 equivalent, preferably 0.9 to 0.99 equivalent, to platinum compound (B). If a small amount of silver sulfate is used, the reaction yield is decreased (Table 1). In the production method of the present invention, the amount of silver contained in the product is 1 ppm or less.

In the present invention, the barium salt can be used in an amount of 0.6 to 1.0 equivalent, preferably 0.75 to 0.95 equivalent, to platinum compound (B). Particularly, 0.9 to 0.95 equivalent of barium salt is preferably used. The amount of the barium hydroxide used significantly affects, particularly, the reaction yield and the amount of barium contained in the product (Table 2 below). With the use of an excess of barium hydroxide, barium is contained in a drug product, while with a small amount of barium hydroxide, the reaction yield is decreased. Although the theoretically necessary amount of barium hydroxide is 1.0 equivalent, a target product can be obtained in a yield of 85% or more even by using 0.75 equivalent of barium hydroxide.

In the present invention, production can be carried out in water or a mixed solvent of water and an alcohol (methanol or ethanol). Although the ratio (ratio by volume) of alcohol (methanol or ethanol) to water in the mixed solvent can be selected from the range of 1/20 to 2/1, production is preferably carried out in water.

The amount of the solvent used in the present invention may be an amount required for maintaining the appropriate fluidity of the reaction substances, and is 5 to 200 times the weight of platinum compound (B).

The present invention is described in detail below with reference to a preferred embodiment in which silver sulfate and barium hydroxide are used as the silver salt and the barium salt, respectively.

Possible methods of adding the reaction substances, platinum compound (B), compound (C), silver sulfate and barium hydroxide include a method in which silver sulfate is added to a solution containing platinum compound (B) and compound (C), and barium hydroxide is then added to the solution; a method in which barium hydroxide is added to a solution containing platinum compound (B) and compound (C), and silver sulfate is then added to the solution. By either of the methods, the target product can be obtained. Methods of adding reaction reagents (silver sulfate and barium hydroxide) and raw materials (platinum compound (B) and compound (C)) include a method of adding the reaction reagents (silver sulfate and barium hydroxide) and the raw materials (platinum compound (B) and compound (C)) without any treatment, and a method of adding dropwise appropriate solutions of the reaction reagents (silver sulfate and barium hydroxide) and the raw materials (platinum compound (B) and compound (C)). The former method is advantageous from the viewpoint of no need for a step of preparing a solution. Although the reaction reagents (silver sulfate and barium hydroxide) and the raw materials (platinum compound (B) and compound (C)) can be added at a temperature of −10° to 60° C., these materials are preferably added at 0° to 40° C. This is because the reaction product is possibly decomposed at 40° C. or higher. At a temperature below 0° C., much time is required for completing reaction, and the productivity thus deteriorates, thereby causing an economical disadvantage.

In the present invention, reaction of platinum compound (B), compound (C), silver sulfate and barium hydroxide produces barium sulfate and silver chloride. These salts can easily be removed by an ordinary solid-liquid separation method such as filtration, centrifugation, etc. A conventional two-step synthetic method requires two separations (silver chloride and barium sulfate) in each step. Particularly, separation of barium sulfate requires much time for precipitating fine particles. However, since the one-step reaction of the present invention produces a mixed salt of barium sulfate and silver chloride, the salts can be separated within a short time with high economical advantage, as compared with a single salt of barium sulfate. As described above, in the one-step reaction of the present invention, since platinum compound (A) can be obtained by using equivalents or less of silver sulfate and barium hydroxide relative to platinum compound (B), there is a low possibility that a drug product contains silver and barium.

The use of the method of the present invention significantly improves the yield to 75 to 80%, in comparison with a conventional method.

The reaction solution obtained by the solid-liquid separation method is concentrated to obtain target platinum compound (A). The compound (A) can be purified by a general method, i.e., column chromatography, recrystallization, or the like.

The dichloroplatinum (II) complex (B) used in the present invention can be obtained by reacting trans-1,2-diaminocylcohexane and potassium chloroplatinate in accordance with the procedure disclosed in Japanese Patent Unexamined Publication No. 61-33192.

In order to secure the quality as a drug, it is necessary to use trans-1,2-diaminocyclohexane having an optical purity higher than the optical purity of a present commercial product of about 99% ee. The inventors found a method of increasing the optical purity of 1,2-diaminocylcohexane. The method is described in detail below.

Optically active trans-1,2-diaminocyclohexane is mixed with an inorganic or organic acid having no optically active point to produce an optically active salt of trans-1,2-diaminocyclohexane, and the resultant salt is recrystallized from a water-soluble organic solvent or a mixed solvent of water and a water-soluble organic solvent.

In further detail, 1-trans-1,2-diaminocyclohexane or d-trans-1,2-diaminocyclohexane is mixed with an acid such as concentrated hydrochloric acid at −20° to 60° C., preferably at 0° to 30° C., in a mixed solvent of water and a water-soluble organic solvent (ethanol, methanol, 1-propanol or 1-butanol) or a water-soluble organic solvent, preferably, in a solvent such as isopropanol, and the resultant salt is separated or dissolved in the same system by heating, cooled and then filtrated off to obtain a salt of trans-1,2-diaminocyclohexane having high optical purity in high yield.

Any acids which can form salts with trans-1,2-diaminocyclohexane and crystallize can be used as the acid having no optically active point. Examples of such acids include inorganic acids such as sulfuric acid, hydrochloric acid, hydroborofluoric acid, and perchloric acid; and organic acids such as maleic acid, phthalic acid, oxalic acid, succinic acid, and acetic acid. It is preferable from the viewpoint of ease of recrystallization to use hydrochloric acid, maleic acid, succinic acid, oxalic acid or sulfuric acid. These acids may be used singly or in combination of at least two acids.

The acid can be used in an amount of 1 to 3 equivalents to trans-1,2-diaminocyclohexane.

As the water-soluble organic solvent for mixing 1,2-diaminocyclohexane and the acid, it is preferable to use a solvent which dissolves an acid, which does not dissolve the salt produced from trans-1,2-diaminocyclohexane and an acid, and which does not chemically deteriorate compounds. Examples of such solvents include tetrahydrofuran, methanol, ethanol, butanol, 1-propanol, and 2-propanol. Methanol, ethanol, 1-propanol, 2-propanol and butanol are preferred, and 2-propanol is particularly preferred.

In the present invention, only the water-soluble organic solvent, or a mixed solvent of the water-soluble organic solvent and water can be used. The mixing ratio (ratio by volume) of the water-soluble organic solvent to water in the mixed solvent is 4 to 8 times, preferably about 6 times. The water-soluble organic solvent used may be a mixture of at least two water-soluble organic solvents.

The crystals of the resultant salt of trans-1,2-diaminocylcohexane can easily be separated by the general solid-liquid separation method such as filtration, centrifugation or the like. The resultant salt can easily be converted to trans-1,2-diaminocyclohexane by using a base such as sodium hydroxide.

[EXAMPLES]

Example 1

Synthesis of [(5S)-3-acetyl-5-methyl-2,4-(3H, 5H)-furandionate-03 04] [(1R, 2R)-cyclohexanediamine-N,N'] platinum (1+) (5S)-3-acetyl-5-methyl-2,4-(3H, 5H)-furandione enolate:

To 160 ml of aqueous solution containing 7.60 g (20.0 mmol) of dichloro(trans-1,2-diaminocyclohexane) platinum (II) and 6.55 (41.9 mmol) of (5S)-methyl-3-acetyltetronic acid, 6.11 g (19.6 mmol) of silver sulfate was added. 54 g (18.5 mmol) of barium hydroxide octahydrate was then added to the resultant mixture, followed by stirring at room temperature for 12 hours. Insoluble substances were filtered off by using a membrane filter of 0.45 mm, and the filtrate was concentrated under reduced pressure by a rotary evaporator. A small amount of methanol was added to the residue, and tetrahydrofuran was then added to the resulting mixture to precipitate colorless crystals. The crystals were filtered off, and washed with tetrahydrofuran. The resulting crystals were dried and then recrystallized from water to obtain 9.90 g of target compound.

The table below shows the relations between reaction of dichloro(trans-1,2-diaminocylcohexane) platinum (II) and (5S)-methyl-3-acetyltetronic acid and the amounts of the reagents used.

TABLE 1

| Amount of silver sulfate relative to compound (B) (equivalent) | Amount of silver contained in product (ppm) | Yield (%) |
|---|---|---|
| 0.98 | 0.545 | 98.6 |
| 0.97 | 0.470 | 93.6 |
| 0.95 | 0.481 | 90.6 |
| 0.925 | — | 86.0 |
| 0.9 | — | 84.7 |
| 0.85 | — | 73.8 |

(The amount of barium hydroxide used was 0.925 equivalent to compound (B).)

TABLE 2

| Amount of barium hydroxide relative to compound (B) (equivalent) | Amount of barium contained in product (ppm) | Yield (%) |
|---|---|---|
| 0.95 | 2.09 | 98.2 |
| 0.925 | 0.545 | 98.5 |
| 0.9 | 0.387 | 98.4 |
| 0.85 | — | 87.0 |
| 0.75 | — | 85.4 |

(The amount of silver sulfate used was 0.98 equivalent to compound (B).)

Example 2

Formation of 1-trans-1,2-diaminocyclohexane maleate:

In ethanol (10 ml), 2.01 g of 1-trans-1,2-diaminocyclohexane (1-form purity 98.7% ee) was dissolved, and an ethanol solution (10 ml) of maleic acid (2.05 g) was added dropwise at the ice temperature. After stirring at room temperature for 2 hours, the resulting mixture was filtered, and the residue was washed with ethanol (20 ml) to obtain 1-trans-1,2-diaminocyclohexane maleate (yield 3.52 g).

To 498 mg of the resultant 1-trans-1,2-diaminocyclohexane maleate, water (0.40 ml) was added, and the resultant mixture was dissolved under heating. To the resultant solution, 11 ml of ethanol was added, and the mixture was cooled to precipitate crystals. The crystals were then filtered off.

Yield: 390 mg (78%)

L-form purity: 99.6% ee

Example 3

Formation of 1-trans-1,2-diaminocyclohexane phthalate:

In ethanol (10 ml), 1.94 g of 1-trans-1,2-diaminocyclohexane (1-form purity 98.7% ee) was dissolved, and an ethanol (20 ml) solution of phthalic acid (2.82 g) was added dropwise at the ice temperature. After stirring at room temperature for 2 hours, the resultant mixture was filtered, and the residue was washed with ethanol (20 ml) to obtain 1-trans-1,2-diaminocyclohexane maleate (yield 4.50 g).

To 504 mg of the resultant 1-trans-1,2-diaminocyclohexane phthalate, water (6 ml) was added, and the resultant mixture was dissolved under heating. To the resultant solution, 21 ml of ethanol was added, and the resultant mixture was cooled to precipitate crystals. The crystals were filtered off.

Yield: 390 mg (77%)

L-form purity: 99.7% ee

Example 4

Formation of 1-trans-1,2-diaminocyclohexane hydrochloride:

In isopropanol (300 ml), 105 g of 1-trans-1,2-diaminocyclohexane (1-form purity 98.7% ee) was dissolved, and a tetrahydrofuran (500 ml) solution of concentrated hydrochloric acid (162 ml) was added dropwise at the ice temperature. After stirring at room temperature for 1 hour, 1000 ml of tetrahydrofuran was added to the resultant mixture, and the mixture was cooled with ice and then filtered. The residue was washed with ethanol to obtain 1-trans-1,2-diaminocyclohexane hydrochloride (yield 170 g).

To 497 mg of the resultant 1-trans-1,2-diaminocyclohexane hydrochloride, water (6 ml) was added, and the resultant mixture was dissolved under heating. To the resultant solution, 3 ml of ethanol was added, and the resultant mixture was cooled to precipitate crystals. The crystals were filtered off.

Yield: 314 mg (63%)

L-form purity: 100% ee

Example 5

Formation of 1-trans-1,2-diaminocyclohexane hydrochloride:

In a mixture of water (2 ml) and isopropanol (2 ml), 5.0 g of 1-trans-1,2-diaminocyclohexane (1-form purity 98.7% ee) was dissolved, and concentrated hydrochloric acid (8 ml) was added dropwise at the ice temperature. After stirring at room temperature for 40 minutes, heated isopropanol (58 ml) was added to the resultant mixture, and the mixture was cooled with ice and then filtered. The residue was washed with ethanol to obtain 1-trans-1,2-diaminocyclohexane hydrochloride.

Yield: 6.56 g (80%)

L-form purity: 99.8% ee

Example 6

To an aqueous solution (180 ml) of the 1-trans-1,2-diaminocylcohexane hydrochloride (104.5 g) synthesized in Example 4, an aqueous solution (180 ml) of potassium hydroxide (62.73 g) was added at the ice temperature, followed by stirring at room temperature for 15 minutes. To the resultant mixture, an aqueous solution (1270 ml) of potassium chloroplatinate (II) (200.0 g) was added, and the resulting mixture was stirred overnight. The precipitated crystals were filtered off under reduced pressure, and washed with water and methanol. The crystals were dried under reduced pressure to obtain dichloro (trans-1,2-diaminocylcohexane) platinum (II).

Yield 179.19 g (97.8%)

To 320 ml of an aqueous solution containing 15.20 g of dichloro (trans-1,2-diaminocyclohexane) platinum (II) and 13.1 g of (5S)-methyl-3-acetyltetronic acid, 12.22 g of silver sulfate was added. 11.68 g of barium hydroxide octahydrate was then added to the mixture, followed by stirring at room temperature for 12 hours. Insoluble substances were then filtered off by using a membrane filter of 0.45 pm, and the filtrate was concentrated by using an evaporator. A small amount of methanol was added to the residue, and tetrahydrofuran was added to the resultant mixture to precipitate colorless crystals. The crystals were filtered off, and washed with tetrahydrofuran. The resulting crystals were then dried.

Yield 25.7 g (93.0%)

The crystals were recrystallized from water to obtain 19.6 g of target compound. (A yield of 77% from 1-trans-1,2-diaminocylcohexane hydrochloride.)

INDUSTRIAL APPLICABILITY

The use of the production method of the present invention is capable of producing a drug product containing very small amounts of heavy metals such as barium and silver in high yield within a short period of time. It is also possible to obtain trans-1,2-diaminocyclohexane useful as a starting material for drugs with high optical purity.

We claim:

1. A method of producing a platinum (II) complex represented by the following formula (A):

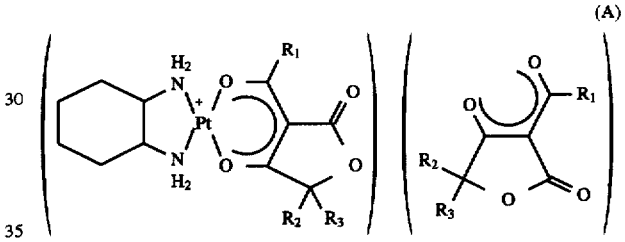

which comprises reacting dichloroplatinum (II) complex represented by the following formula (B):

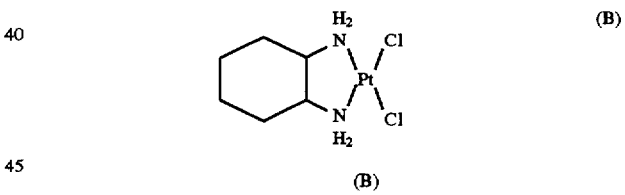

and a tetronic acid derivative represented by the following formula (C):

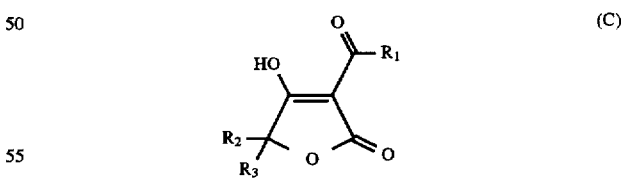

wherein $R_1$ represents a lower hydrocarbon group having 1 to 3 carbon atoms, and $R_2$ and $R_3$ each represents a hydrocarbon atom or a lower hydrocarbon group having 1 to 3 carbon atoms in the presence of a silver salt and a barium salt.

2. A method of producing a platinum (II) complex according to claim 1, wherein silver sulfate is used as the silver salt.

3. A method of producing a platinum (II) complex according to claim 1, wherein the silver salt is used in an amount of 0.9 to 0.99 equivalent with to the dichloroplatinum (II) complex represented by formula (B).

4. A method of producing a platinum (II) complex according to claim 1, wherein barium hydroxide is used as the barium salt.

5. A method of producing a platinum (II) complex according to claim 1, wherein the barium salt is used in an amount of 0.75 to 0.95 equivalent with respect to the dichloroplatinum (II) complex represented by formula (B).

6. A method of producing a platinum complex represented by the following formula (A):

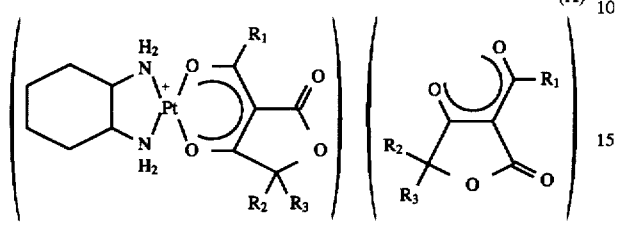

(A)

which comprises reacting an optically active 1-trans-1,2-diaminocyclohexane with potassium chloroplatinate to produce a dichloroplatinum (II) complex represented by the following formula (B):

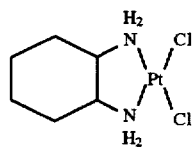

(B)

and reacting with a tetronic acid derivative represented by the following formula (C):

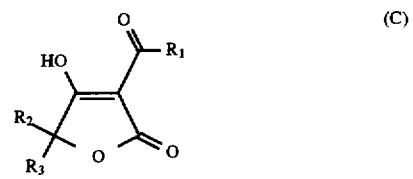

(C)

in the presence of a silver salt and a barium salt.

* * * * *